United States Patent [19]
Dobkowski et al.

[11] Patent Number: 5,833,973
[45] Date of Patent: Nov. 10, 1998

[54] CROSSLINKED ELASTOMERIC SILICONES IN AQUEOUS EMULSION COSMETIC COMPOSITIONS

[75] Inventors: Brian John Dobkowski, Shelton; Alexander Paul Znaiden, Trumbull; Michael Charles Cheney, Fairfield; Walter Rose, New Haven; Salvador Pliego, Hamden, all of Conn.

[73] Assignee: Chesebrough-Pond's USA Co., Division of Conopco, Inc., Greenwich, Conn.

[21] Appl. No.: 821,132

[22] Filed: Mar. 20, 1997

Related U.S. Application Data

[60] Provisional application No. 60/020,765, Jun. 28, 1996.

[51] Int. Cl.$^6$ ............................................. A61K 7/48
[52] U.S. Cl. .................. 424/18.08; 424/401; 514/844; 514/845; 514/846; 514/941
[58] Field of Search ................ 424/401, 78.08; 514/844–846, 941

[56] References Cited

U.S. PATENT DOCUMENTS

| | | |
|---|---|---|
| 4,720,353 | 1/1988 | Bell . |
| 4,742,142 | 5/1988 | Shimizu et al. . |
| 4,980,167 | 12/1990 | Harashima et al. . |
| 4,987,169 | 1/1991 | Kuwata et al. . |
| 5,143,722 | 9/1992 | Hollenberg et al. . |
| 5,266,321 | 11/1993 | Shukuzaki et al. . |
| 5,280,019 | 1/1994 | Klimisch . |
| 5,387,417 | 2/1995 | Rentsch . |

FOREIGN PATENT DOCUMENTS

96/018374   6/1996   WIPO .

OTHER PUBLICATIONS

GE Silicones Material Safety Data Sheet Jul. 24, 1996.

*Primary Examiner*—Jyothsna Venkat
*Attorney, Agent, or Firm*—Milton L. Honig

[57] ABSTRACT

A skin treatment composition is provided which includes a crosslinked non-emulsifying siloxane elastomer, a volatile siloxane and at least 50% by weight of water. Inclusion of the elastomer provides a unique liquid/powdery feel when rubbed into the skin.

6 Claims, No Drawings

CROSSLINKED ELASTOMERIC SILICONES IN AQUEOUS EMULSION COSMETIC COMPOSITIONS

BACKGROUND OF THE INVENTION

This application claims benefit of USC Provisional Application No. 60/020,745, filed Jun. 28, 1996.

1. Field of the Invention

The invention relates to aqueous emulsion cosmetic compositions whose properties are enhanced by incorporation of crosslinked elastomeric silicones.

2. The Related Art

Emollients including organic esters and hydrocarbons, especially petrolatum, have long been used medicinally as skin conditioning agents. These substances are second only to water as moisturizing ingredients of choice. They function primarily as an occlusive barrier. The water content of the outer layers of human skin stratum corneum is a controlling factor in the appearance of dry skin symptoms. When the stratum corneum contains an adequate amount of water within the range of ten to twenty percent, the skin remains flexible. However, when the water content falls below ten percent the stratum corneum often becomes brittle and rough and can exhibit scaling and cracking.

The stratum corneum receives its water from the deep layers of the epidermis by diffusion or when it is brought into direct contact with water. The diffusion process is controlled by the water content of the skin as well as the concentration gradient. In a very dry environment, the water loss from the external skin layers can be significant and often exceeds the rate of replacement by diffusion. An occlusive or semi-occlusive barrier substance placed on the surface of the skin acts to retard water loss to the environment. It also allows the skin surface to rehydrate via a diffusion mechanism.

While there are many effective and economical skin conditioning agents, they nevertheless suffer from certain disadvantages.

Often the emollient types are delivered as water in oil emulsions. It is difficult to attain the critical formula balance between oil and water phases to an extent sufficient to ensure long term storage stability. One part of this critical balance is the internal phase volume. A critical volume must be obtained to maximize the chemical and physical interactions which produce and stabilize the system. If this critical volume is not balanced properly the product may suffer from viscosity change and eventual phase separation. Usually the optimum volume is quite large which limits the external phase volume size, and gives the system a draggy unfavorable slow break attribute. This critical internal phase volume restriction can reduce functionality and add unfavorable feel characteristics.

Anhydrous systems avoid emulsion stability problems. Unfortunately other aesthetic issues arise with anhydrous systems. Not all oily phase materials are compatible at high concentration. Moreover, occlusive agents such as petrolatum are relatively greasy. They suffer the disadvantage of transfer onto clothing and are not easily removed from the skin by washing with soap. Neither do they allow for adequate penetration into the epidermis.

U.S. Pat. No. 5,387,417 (Rentsch) reports obtaining cosmetically acceptable, translucent moisturizing lotions through emulsification of a petrolatum base with a crosslinked organopolysiloxane-polyoxyalkylene emulsifier. According to the disclosure, not only is compatibility achieved but this siloxane allows for matching of refractive indices for the continuous and discontinuous phases.

U.S. Pat. No. 5,280,019 (Klimisch) reports compositions which enhance the absorption and retention of moisturizer on the skin. These results are achieved through use of an organosilicon compound which is a carboxy functionalized polysiloxane or its metal carboxylate salt.

Evident from the foregoing art is that certain types of polysiloxanes incorporating hydrophilic functionality, e.g. polyoxyalkylene or carboxylate units, can assist in the emulsification of oily phases. Indeed these disclosures suggest the requirement for hydrophilic functionality on the silicones. Incorporation of hydrophilic groups for emulsification unfortunately detracts from the ability of silicones to provide a soft, silky afterfeel. These prior art hydrophilic silicones also do not fully solve oil and water phase compatibility problems. New systems are needed to carry relatively high levels of water and/or aqueous based moisturizing ingredients. Also necessary are silicones that can achieve a smoother emulsion break to maximize positive sensory/feel attributes when the emulsions are rubbed into the skin.

Accordingly, it is an object of the present invention to provide a skin treatment composition which in emulsion form provides improved skinfeel properties.

Another object of the present invention is to provide a skin treatment composition which in emulsion form exhibits sufficient stability to allow for long term storage without phase separation.

Yet another object of the present invention is to provide a skin treatment composition which allows formulation of relatively high levels of water in a water-in-oil emulsion.

Still another object of the present invention is to provide a skin treatment composition which in emulsion form achieves a smooth emulsion break when rubbed into the skin.

These and other objects of the present invention will become more readily apparent from consideration of the following summary and detailed description.

SUMMARY OF THE INVENTION

A skin treatment composition is provided which includes:
(i) from 0.1 to 30% of a crosslinked non-emulsifying siloxane elastomer;
(ii) from 10 to 80% of a volatile siloxane; and
(iii) from 50 to 85% by weight of water.

Elastomers of the present invention are formed from a divinyl compound reacting with Si-H sites on a polysiloxane backbone. Most preferred of the elastomers are divinyl polysiloxanes crosslinked at Si-H sites on a molecularly spherical MQ resin. Cyclomethicones are the preferred volatile siloxanes.

Although not to be bound by theory, it is believed the volatile siloxane acts as an external phase while dispersing an otherwise insoluble crosslinked siloxane elastomeric powder. Upon application of this system to the skin, the volatile siloxane evaporates while the aqueous phase being more compatible with skin fluids, becomes entrapped in the upper layer of the stratum corneum. Siloxane elastomer, not being compatible with these body fluids, remains on the surface of the skin. Since this elastomer was completely dispersed in the volatile siloxane, it is deposited in a very uniform layer on the skin. The thick three-dimentionally crosslinked siloxane elastomer film now functions as a layer between the insoluble aqueous/lipid context of the skin and the external environment.

DETAILED DESCRIPTION OF THE INVENTION

Now it has been found that a crosslinked non-emulsifying siloxane elastomer in combination with a volatile siloxane and an aqueous phase result in a highly stable system and deliver an unusually soft, silky afferfeel to skin.

Crosslinked non-emulsifying siloxane elastomers are a first essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si-H linkages of a polysiloxane backbone such as a molecularly spherical MQ resin. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries ordinarily are further processed by subjecting them to a high pressure (approximately 5,000 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.1 to 30%, optimally from 1 to 15%, most preferably from 3 to 10% by weight.

Compositions of the invention may optionally contain a skin conditioning agent. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range anywhere from 1 to 50%, preferably from 10 to 40%, optimally from 25 to 35% by weight.

Exfoliants according to the present invention may be selected from alpha-hydroxycarboxylic acids, beta-hydroxycarboxylic acids and salts of these acids. Most preferred are glycolic, lactic and salicylic acids and their ammonium salts.

A wide variety of $C_2$–$C_{30}$ alpha-hydroxycarboxylic acids may be employed. Suitable examples include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and parafins such as isohexadecane (e.g. Permethyl 99® and Permethyl 101®).

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Amounts of the skin conditioning agent may range from 1 to 50%, preferably from 3 to 25%, optimally from 5 to 20% by weight.

A second essential element of the present invention is that of a volatile siloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from 0.1 to 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); SF1202 (manufactured by General Electric).

Amounts of the volatile siloxane will range from 10 to 80%, preferably from 20 to 70%, optimally from 30 to 65% by weight.

Cosmetic compositions of the present invention will contain substantial levels of water. Emulsions of the present invention will contain water in amounts ranging from 50 to 85%, preferably from 55 to 70% by weight. The emulsions may be of the oil-in-water, water-in-oil or duplex variety. Most especially, the invention is concerned with the water-in-oil variety. Aqueous to oily phases will range in weight from 10:1 to 1:10, preferably from 1:1 to 2:1, optimally from 1:1 to 1.5:1.

Most preferable for the present invention are water-in-oil emulsions having a high internal (water) phase volume.

Surfactants will be a further component of compositions according to the present invention. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as Cocamidopropyl betaine).

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Minor adjunct ingredients may also be included such as fragrances, antifoam agents, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

This Example illustrates an aqueous emulsion skin treatment composition typical of the present invention. Components listed in the Table below are added together in a vessel at 60° C. and mixed with a homogenizing agitator. Thereafter they are subjected to sonolation at 800–1,000 psi for five to ten minutes. The resultant product is a non-greasy lotion with a very silky afterfeel.

TABLE I

| COMPONENT | WEIGHT % |
| --- | --- |
| Glycerin | 9.5 |
| Gransil SR-CYC | 20 |
| Water | 50 |
| DC 244 Fluid ® | 20 |
| Polysorbate 20 | 0.5 |

EXAMPLE 2

A series of formulations were prepared to evaluate the effect of water upon emulsion stability and the quality of elastomer/siloxane systems. Table II lists the compositions and Table III describes physical properties of the resultant emulsions. Only the 50% aqueous system exhibited a satisfactory emulsion quality.

TABLE II

| | Formulation (weight %) | | | |
| --- | --- | --- | --- | --- |
| COMPONENTS | A | B | C | D |
| Demineralized water | 50 | 40 | 30 | 20 |
| Polysorbate 20 | 1.1 | 1.1 | 1.1 | 1.1 |
| Carbomer (2% in water) | 0.4 | 0.4 | 0.4 | 0.4 |
| Triethanolamine | 0.5 | 0.5 | 0.5 | 0.5 |
| Vinyl dimethicone/methicone crosspolymer (25% active in cyclomethicone) | 24 | 24 | 24 | 24 |
| Cyclomethicone | 24 | 34 | 44 | 54 |

| | FORMULATION | | | |
| --- | --- | --- | --- | --- |
| RESULTS | A | B | C | D |
| Appearance | Creamy and White | Translucent | Translucent | Clear |
| Emulsion Quality | GOOD water in silicone emulsion | FAIL mixed w/s - s/w emulsion slight phase separation | FAIL complete phase separation | FAIL complete phase separation white particulates suspended |

EXAMPLES 3–11

Illustrated in the Table below are a series of aqueous emulsion formulations according to the skin treatment compositions of the present invention of the present invention. These examples can be prepared in a manner similar to that described in Example 1.

TABLE III

| COMPONENT | EXAMPLE NO. (WEIGHT %) | | | | | | | | |
| --- | --- | --- | --- | --- | --- | --- | --- | --- | --- |
| | 3 | 4 | 5 | 6 | 7 | 8 | 9 | 10 | 11 |
| Petrolatum | 2 | 10 | — | — | — | — | — | 10 | — |
| Isohexadecane | 8 | — | 10 | — | — | — | — | — | — |
| Glycerin | — | — | — | 10 | — | — | 5 | 10 | 5 |
| Propylene Glycol | — | — | — | — | 10 | — | — | — | — |
| Polyethylene Glycol | — | — | — | — | — | 10 | 5 | — | — |
| Crosslinked Siloxane Elastomer | 20 | 20 | 20 | 10 | 10 | 10 | 10 | 15 | 10 |
| Polysorbate 20 | 0.8 | 0.8 | 0.8 | 0.8 | 0.8 | 0.8 | 0.8 | 0.8 | 0.8 |
| Water | 60 | 60 | 60 | 50 | 50 | 50 | 50 | 50 | 70 |
| Cyclomethicone | 10 | 10 | 10 | 30 | 30 | 30 | 30 | 15 | 10 |

The foregoing description and Examples illustrate select embodiments of the present invention. In light thereof, various modifications will be suggested to one skilled in the art, all of which are within the purview and spirit of this invention. What is claimed is:

1. A skin treatment composition comprising:
   (i) from 0.1 to 30% of a vinyl dimethicone/methicone cross polymer;
   (ii) from 10 to 80% of a volatile siloxane; and
   (iii) from 50 to 85% by weight of water.

2. The composition according to claim 1 further comprising from 1 to 50% of a skin conditioning agent selected from the group consisting of humectants, exfoliants, emollients and mixtures thereof.

3. The composition according to claim 2 wherein the emollient is a hydrocarbon.

4. The composition according to claim 3 wherein the hydrocarbon is petrolatum.

5. The composition according to claim 2 wherein the humectant is a polyol selected from the group consisting of glycerin, propylene glycol, polyethylene glycol and mixtures thereof.

6. The composition according to claim 2 wherein the exfoliant is selected from the group consisting of alpha-hydroxycarboxylic acid, beta-hydroxycarboxylic acid and salts thereof.

* * * * *